Figure 1:
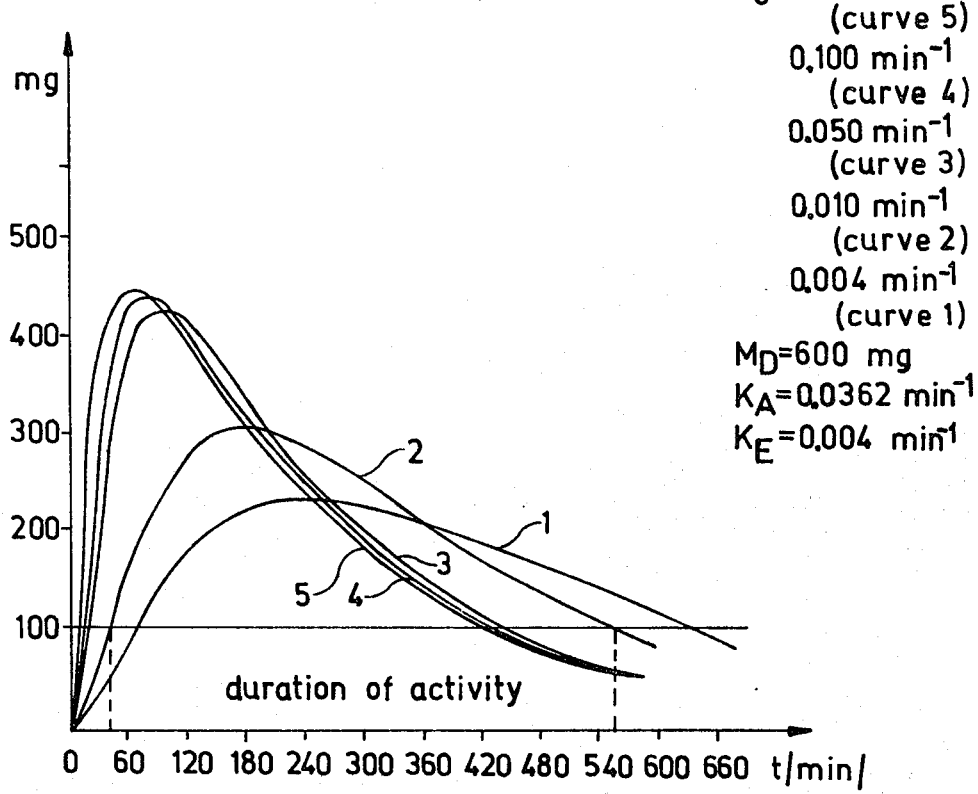

United States Patent [19]

Horvath et al.

[11] 4,434,152
[45] Feb. 28, 1984

[54] TIME-RELEASE

[75] Inventors: Tibor Horváth; Ágnes Udvardy; Ágoston Dávid, all of Budapest; Katalin Mármarosi née Kellner, Biatorbágy, all of Hungary

[73] Assignee: CHINOIN Gyogyszer es Vegyeszeti Termekek Gyara Rt., Budapest, Hungary

[21] Appl. No.: 372,049

[22] Filed: Apr. 26, 1982

[30] Foreign Application Priority Data

Apr. 28, 1981 [HU] Hungary ........................... 1092

[51] Int. Cl.$^3$ ...................... A61K 9/22; A61K 9/24
[52] U.S. Cl. ........................................ 424/19; 424/21; 424/32; 424/33
[58] Field of Search ........................... 424/19–22, 424/32, 33

[56] References Cited

U.S. PATENT DOCUMENTS

| 2,702,264 | 2/1955 | Kläul | 424/33 |
| 2,918,411 | 12/1959 | Hill | 424/80 |
| 3,097,144 | 7/1963 | Banker | 424/33 |
| 3,102,845 | 9/1963 | Fennell | 424/80 |
| 3,325,365 | 6/1967 | Hotko et al. | 424/33 |
| 3,554,767 | 1/1971 | Daum | 424/33 |
| 4,091,091 | 5/1978 | Terrill | 424/80 |
| 4,143,129 | 3/1979 | Marsden | 424/80 |
| 4,228,161 | 10/1980 | Shen | 424/274 |
| 4,234,586 | 11/1980 | Hermecz et al. | 424/248.56 |
| 4,264,573 | 4/1981 | Powell et al. | 424/80 |

FOREIGN PATENT DOCUMENTS

| 1380171 | 1/1975 | United Kingdom | 424/80 |
| 1499672 | 2/1978 | United Kingdom | 424/80 |

OTHER PUBLICATIONS

"Schriftenreihe Anwendungstechnik Pigmente", Grundlagen und Anwendungen von AEROSIL Teil 6 AEROSIL in Pharmazie und Kosmetik pp. 10–27, Nummer 49, DEGUSSA.
"Schriftenreihe Anwendungstechnik Pigmente", AEROSIL in der Pharmazie und Kosmetik Degussa.
"AEROSIL In Pharmazie und Kosmetik", Dr. Horst Ferch/Grundlagen und Anwendungen einer durch Flammenhydrolyse gewonnenen Kieselsäure.

Primary Examiner—Shep K. Rose
Attorney, Agent, or Firm—Karl F. Ross; Herbert Dubno

[57] ABSTRACT

Time-release pharmaceutical compositions, suitable for oral administration, are disclosed, which comprise as active ingredient 50 to 70% by weight of a compound of the formula (I)

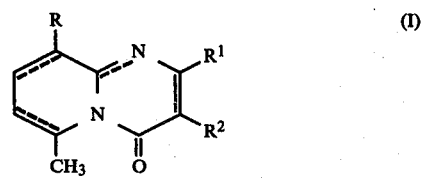

or the formula (Ia)

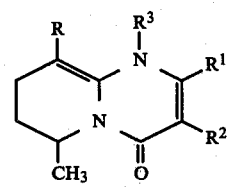

wherein
R is hydrogen or —CH$_2$COOH,
R$^1$ is hydrogen or alkyl having 1 to 4 carbon atoms,
R$^2$ is alkyl having 1 to 4 carbon atoms, alkoxycarbonyl having 2 to 5 carbon atoms, carbamoly or ureido,
R$^3$ is hydrogen or methyl, and the dotted line stands for two hydrogens or another bond, or a pharmaceutically acceptable acid addition or quaternary ammonium salt thereof, and which further include 4 to 8% by weight of a hydrophobic substance with a great specific surface;
7 to 12% by weight of a lipoid;
8 to 12% by weight of a polyoxy compound;
4 to 9% by weight of a binding agent; and
0.5 to 4% by weight of an acid stabilizer.

12 Claims, 2 Drawing Figures

TIME-RELEASE ORAL PHARMACEUTICAL COMPOSITIONS

The present invention relates to the preparation of oral time-release pharmaceutical compositions (tablets or dragees) which are not sensitive to the pressure used at compression within a wide range and which contain compounds of the formula I

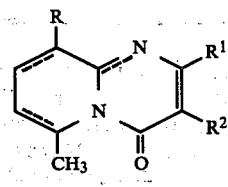

as active ingredient.

In the last decades the research work in the field of time-release pharmaceutical compositions administered orally has become more intensive. The increased activity in this field is due to the advantages of this type of pharmaceutical composition:

1. When using a time-release composition the concentration of the active ingredient in the blood is almost constant, thus the therapy is more successful.
2. The possibility of irregular administration is reduced and thus the danger of the interruption of the therapy and of the failure of the therapy is smaller.
3. The application of the medicine is more comfortable.
4. The active ingredients may be utilized more economically.

There are several processes for the preparation of time-release compositions.

The time-release activity may be achieved physiologically e.g. by blocking the enzyme metabolizing the active ingredient, chemically e.g. by conversion to a derivative which becomes eliminated more slowly and by physical methods. Most of the physical methods comprise the embedding of the active ingredient in a matrix of various compositions and various properties or the coating of the active ingredient. While the physiological and chemical methods are specific for the active ingredient, the physical methods can be applied generally as they influence the dissolution of the active ingredient in the gastrointestinal tract. This means the decrease of the rate of the dissolution process under the conditions of the digestive system. The extent of this decrease can be planned by pharmaceutical engineering with biologically optimal effectivity. When preparing tablets or dragees the composition or granulate has to meet several technical requirements, such as particle size, humidity, flowability. The thus prepared granulate (powder mixture) is pressed to tablets or dragées.

In the course of large scale production the compressing pressure should always have the prescribed value, so as to obtain a batch of equal biological quality, this criterium, however cannot be ensured. The object of the invention is to prepare such tablets or dragees, which due to their structure react on small changes of the compressing pressure by having unchanged dissolution properties.

The invention relates to a process for the preparation of oral time-release tablets and dragees containing as active ingredient a compound of the Formula I

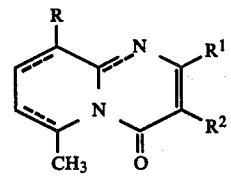

wherein
R stands for hydrogen or —CH$_2$—COOH,
R$^1$ stands for hydrogen or alkyl having 1 to 4 carbon atoms,
R$^2$ stands for alkyl having 1 to 4 carbon atoms, alkoxy carbonyl containing 2 to 5 carbon atoms or carbamoyl and
the dotted line stands for an optionally present double bond—or acid addition salts or quaternary ammonium salts thereof and optionally another known active ingredient comprising admixing 50 to 70% by weight of active ingredient of the formula I—wherein R, R$^1$, R$^2$ and the dotted line are as given above—or an acid addition salt, or a quaternary ammonium salt thereof and optionally another known active ingredient with 4 to 8% by weight of a hydrophobic substance of great specific surface, 7 to 12% by weight of a lipoid, 8 to 12% by weight of a polyoxy compound, 4 to 9% by weight of a binding material, 0.5-4% by weight of an acidic stabilizer and if desired with filling agents, diluents, lubricants and other excipients, and preparing tablets or dragées suitable for oral administration.

In the process according to the invention preferably 1,6-dimethyl-3-carbethoxy-4-oxo-6,7,8,9-tetrahydro-homopyrimidazolium-metosulphate (Rimazolium-methylsulphate), 2,6-dimethyl-3-ethyl-4-oxo-4H-pyrido[1,2-a]pyrimidinehydrochloride (CH-150), 2,6-dimethyl-3-ethyl-4-oxo-1,6,7,8-tetrahydro-4H-pyrido[1,2-a]pyrimidine hydrochloride, 1,6-dimethyl-3-ureido-4-oxo-1,6,7,8-tetrahydro-4H-pyrido[1,2-a]pyrimidine (CH-127) or 6-methyl-9-carboxymethyl-4-oxo-6,7,8,9-4H-pyrido[1,2-a]pyrimidine (CH-123) are used. As hydrophobic substance of great specific surface colloidal silicic acid and hydrophobic colloidal silicic acid may be applied.

As lipoids higher fatty acids or derivatives thereof, preferably stearic acid and as polyoxy compounds starch, and as binding agent polyvinyl pyrrolidone vinyl acetate and as stabilizer betaine in hydrochloric acid or citric acid are suitable.

A test series was performed with a dragée composition according to the invention containing an active ingredient of the formula I. The breaking strength of randomly chosen 40 dragées was measured on an Erweka apparatus.

The results are given in Erweka kg units with order of the measurements:
10; 12.25; 12; 10.5; 12.75; 9.75; 9; 8.75; 9.5; 9.5; 10.5; 9.5; 11.25; 12; 12.5; 9.75; 10; 10.75; 9.5; 10; 8.5; 8.5; 10.5; 11.25; 10; 11; 11.75; 9.5; 8.75; 12; 10; 9; 11.25; 10.25; 10; 7.25; 11.5; 8.5; 10.25; 11.25.

Each piece of another batch had a breaking strength of above 15 Erweka kg. Another test series was performed to clarify the relation between the strength of the dragées and the dissolution properties thereof. The dragée-cores were crushed and the IV. sieve fraction was pressed by a Korsch tabletting machine to bi-convex tablets. The tablets of various breaking strength were prepared by a suitable change of the pressing power.

Thus tablets of 4–5, 9–10 and 10–12 kg. Erweka breaking strength were obtained. The dissolution tests were performed with tablets of identical height and weight from all the three samples. The dissolution was investigated in artificial gastric juice in an Erweka ZT-4 apparatus.

The results are shown in the following Table:

| Breaking strength (Erweka kg.) | Dissolution constant (minute$^{-1}$) |
|---|---|
| 4–5 | 0.017 |
| 9–10 | 0.007 |
| 10–12 | 0.002 |

When evaluating the results it is obvious that a given tablet or dragee can be regarded as biologically optimal in a qualitative requirement system if the rate of release of the active ingredient remains within acceptable limits and these limits can be supported by therapeutical experiments.

On the basis of our test results we tried to find a composition and a process for the preparation thereof which is an oral product having optimal biological dissolution properties and long-lasting activity independently on the compressing pressure by which the tablet or dragée core had been prepared.

The retard dragée was planned by a computer-program of a mathematical disclosure elaborated for a pharmacokinetical model. The correlation between the active ingredient concentration in the blood and the time after administration of the drug was studied on a pharmacokinetical model consisting of a three-step consecutive process described by a mathematical disclosure (Acta Pharm. Hung. 45. 225–236, 1975). An ALGOL program was used which was prepared for an ICL 1903 computer. The required pharmacokinetical parameters (such as resorption rate constant, elimination rate constant) can be determined by method known per se.

Pharmacokinetical parameters of the model Rimazolium methylsulphate:
$K_A = 0.0362$ min$^{-1}$ (resorption rate constant)
$K_E = 0.0044$ min$^{-1}$ (elimination rate constant)
On the basis of the mathematical solution brutto blood level curves were plotted (FIG. 1.).

As it can be seen in the figure the dissolution constant ($K_o$) changed by almost three orders of magnitude ensuring thus an "optimal duration of activity" in case of $K_o = 0.01$ min$^{-1}$. This is based on the empirical experience that the 100% effective dosage (DE$_{100}$) can be observed at 100 mg. brutto blood level.

By means of this planning method we unambiguously determined the dissolution constant of the biologically optimal time release oral drug form: 0.01 min$^{-1}$.

As mentioned above the release of active ingredient from the commercially available registered Probon dragee depends to a great extent on the tabletting pressure during tabletting. As it is difficult and uncertain to keep the pressing parameters in the course of the large scale production, the therapeutical effectivity cannot be solved well with the composition now available. During our experimental work we regarded this registered Probon dragee on a referential basis, and we searched the composition by several test series which gives a solution of the problem by changing the quantitative ratio of the registered excipients.

The components of the registered Probon dragée for 1.0 kg. of granulate:

| | |
|---|---|
| Rimazolium methylsulphate | 750.0 g. |
| betaine in hydrochloric acid | 7.5 g. |
| colloidal silicic acid | 12.5 g. |
| hydrophobic colloidal silicic acid (Aerosil R-972) | 20.0 g. |
| microcrystalline cellulose | 122.5 g. |
| polyvinylpyrrolidone vinyl acetate (PVP-VA) | 25.0 g. |
| stearine | 62.5 g. |

Rimazolium methyl sulphate was homogenized with betaine in hydrochloric acid (a compound hydrolyzing upon the effect of acid) with colloidal or hydrophobic colloidal silicic acid (hydrophobic excipients of great specific surface) and with microorystalline cellulose (polyoxy compound). Polyvinylpyrrolidone vinyl acetate (tabletting binding material) and stearine (lubricating hydrophobic excipient) were dissolved in isopropyl alcohol and the homogenizate is kneaded with the solution and it is granulated by method known per se. After drying the granulate is compressed to tablets on a Knorsch tabletting machine by two kinds of compressing pressure.

The entire humidity content of the obtained tablets was less than 2%. The samples were prepared as described above and tabletted. For our model tests we prepared a granulate series, in which all samples contained 12% of stearine, but the hydrophobic colloidal silicic acid and PVP-VA concentration of each sample were varied in increments of 1% over the concentration in the original sample. The granulate samples were compressed to tablets by changing the compressing pressure so as to obtain tablets having 4–5 and 9–10 Erweka kg. breaking strength.

Tablets of equal height and weight were then selected and a dissolution test was performed on Erweka ZT-4 dissolution testing equipment.

The change of the concentration of the released active ingredient was followed as a function of time by subjecting samples taken in various time intervals in artificial gastric juice (Ph. Hg. VI. Vol. I. page 252) to spectrophotometry. The dissolution rate constant of the active ingredients of the samples was determined by methods known per se. The results are shown in the following table.

| Concentration of the excipient in the tablet % | | Strength (Erweka kg.) | Dissolution constant $K_0$ (min$^{-1}$) |
|---|---|---|---|
| aerosil R-972 | PVP-VA | | |
| 0.5 | 1.0 | 4–5 | 0.089 |
| | | 9–10 | 0.026 |
| 1.5 | 2.0 | 4–5 | 0.051 |
| | | 9–10 | 0.030 |
| 2.5 | 3.0 | 4–5 | 0.047 |
| | | 9–10 | 0.047 |
| 3.5 | 4.0 | 4–5 | 0.041 |
| | | 9–10 | 0.041 |
| 4.5 | 5.0 | 4–5 | 0.037 |
| | | 9–10 | 0.037 |
| 5.5 | 6.0 | 4–5 | 0.043 |
| | | 9–10 | 0.024 |
| 6.5 | 7.0 | 4–5 | 0.010 |
| | | 9–10 | 0.010 |

The table shows that the granulate series from which the tablets were compressed, change the dissolution properties less and less in spite of having increased the compressing pressure to a double value. It also shows, that the dissolution constant of the composition consisting of 6.5% aerosil R-972 and 7.0% PVP-PA amounts to 0.01 $K_o$, i.e. to the value which had been indicated as a target when planning the tests. The whole composition of the biologically optimal mixture prepared in our experiment related to 1 kg. of granulate:

| Rimazolium methylsulphate | 634.8 g. |
|---|---|
| betaine in hydrochloric acid | 6.3 g. |
| colloidal silicic acid | 10.6 g. |
| hydrophobic colloidal silicic acid | 67.3 g. |
| microcrystalline cellulose | 103.6 g. |
| polyvinyl pyrrolidone vinyl acetate | 71.8 g. |
| stearine | 105.6 g. |

From the above components 15 000 pieces of bi-convex tablets were compressed under large scale conditions by three kinds of pressure. Each tablet contained 600 mg. of Rinazolium methylsulphate. Thus samples having 4–6, 9–11 and >20 Erweka kg. breaking strength samples were obtained, which well demonstrated the possible errors in a batch, i.e. the possible deterioration of the "biological quality" as mentioned above.

Dissolution test was performed as described above by using a sample collection selected from a normally prepared batch by modern methods.

The results are given in the following table:

| Breaking strength of the tablets (Erweka kg.) | The obtained dissolution constants in vitro (min$^{-1}$) | |
|---|---|---|
| | Limit values | Average |
| 4–6 | 0.011–0.017 | 0.014 |
| 9–11 | 0.009–0.011 | 0.010 |
| 20 | 0.009–0.011 | 0.010 |

The obtained values of the dissolution constants show, that the release of the active ingredients from a dragée core of the above composition is not influenced by the tabletting pressure.

Human preclinical pharmacokinetical investigation of biologically formulated homopyrimidazole derivative Pharmacokinetical studies were performed on human patients in a test of twice six persons by using a single dosage of retard Probon dragée (600 mg.) and by using twice a single dosage of commercially available Probon dragée (300 mg.). The blood samples were examined after 1, 3, 5 and 7 hours by determining MZ-211 content (an effective metabolite formed immediately from Rimazolium in the blood).

Figure 2:
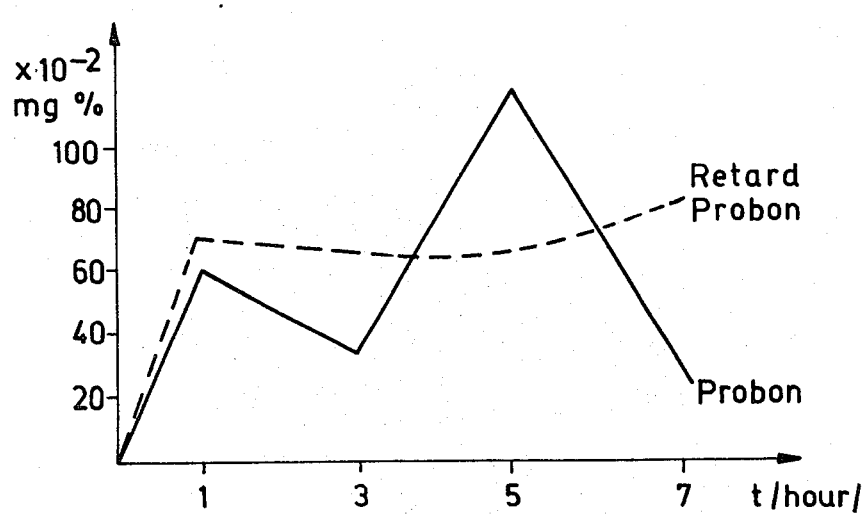

The results are shown in FIG. 2.

Qualitative evaluation of preclinical tests

1. The appearance of the activity of both compositions (about a quarter of an hour), takes substantially the same time.
2. At the end of the examined time span by the seventh hour the blood level of the time release Probon is more than twice as high as the blood level of the control Probon, which is not time release.
3. The blood concentration curve of the time release Probon is during 1–7 hours substantially constant within a range from 55 to 68.10$^{-2}$ mg/%.
4. In the unexamined time interval the blood concentration presumably decreases under the effective level between 10 to 12 hours in the case of the time-release form.
5. These data correspond well to the character of the curves obtained by computer.

According to the process of the invention orally administrable drugs, preferably tablets or dragées may be prepared. According to a preferred method of the invention the homopyrimidazole active ingredient is homogenized with 8–12% polyoxy compound, preferably 10% microcrystalline cellulose, 0.5–3.5% compound hydrolyzing upon the effect of an acid, preferably 0.6% betaine in hydrochloric acid or 3.5% citric acid, 4–8% excipient of great specific surface, preferably 1% colloidal silicic acid and 6.5% hydrophobic colloidal silicic acid, 7–12% lubricant, preferably 10.5% stearic acid, and preferably 7% polyvinyl pyrrolidone vinyl acetate tabletting excipient whereafter the mixture is wet granulated and dried.

The whole humidity content of the prepared granulate is optimal up to 2%.

The correlation between the humidity content of the retard homopyrimidazole tablets and the stability thereof was performed by a heat treatment of dragee core of various humidity content. The samples were kept in a hermetically closed vessel for 14 days at 60° C. and the following results were obtained:

| Humidity content % | Colouration |
|---|---|
| 0.54 | φ |
| 2.44 | + |
| 3.14 | ++ |
| 6.44 | +++ |

Symbols:
+ slight discoloration
++ discoloration (it becomes yellow)
+++ intensive discoloration The humidity content of the dragée cores is optimal up to 2%. The keeping and heat treating the dragée cores of humidity content not exceeding 2% in a hermetically closed vessel for 30 days at various temperatures the active ingredient content changed related to the starting value of 100% as follows.

| | Active ingredient % related to the control |
|---|---|
| 40° C. 30 days | 100.9 |
| 50° C. 30 days | 98.7 |
| 60° C. 30 days | 97.1 |

On the basis of the above results the composition can be stored without indicating the storage time at 20° C. (5 years guarantee time) as calculated by the prediction kinetical method (R. Dolique: Il Farmaco 20, No. 3. 119–146 1965).

Further details of the invention can be found in the following Examples which serve merely for illustration and not for limitation.

EXAMPLE 1

Preparation of time-release Probon dragee core containing 600 mg. of active ingredient

| 1 Dragée core | |
|---|---|
| I. Rimazolium methyl sulphate | 600.0 mg. |

-continued

| | | |
|---|---|---|
| | betaine in hydrochloric acid | 6.0 mg. |
| | colloidal silicic acid | 10.0 mg. |
| | hydrophobic silicic acid | 63.9 mg. |
| | microcrystalline cellulose | 97.9 mg. |
| II. | Polyvinyl pyrrolidone vinyl acetate | |
| | stearine | 99.9 mg. |
| | | 945.5 mg. |
| | Dragée shell | |
| | talc | 47.8 mg |
| | polyvinyl pyrrolidone vinyl acetate | 15.0 mg. |
| | methyl cellulose | 15.0 mg |
| | titanium dioxide | 7.7 mg. |
| | polyoxyethylene 6000 | 2.0 mg. |
| | | 87.5 mg. |

Technology

According to the size of the desired batch the Rimazolium methyl sulphate in the required amount, the microcrystalline cellulose, hydrophobic silicic acid, colloidal silicic acid and the thoroughly pulverized betaine in hydrochloric acid are homogenized in a working apparatus (I). The suitable amount of polyvinyl pyrrolidine vinyl acetate and stearine are dissolved in isopropanol (II). The homogenizate I is kneaded with the solution II and the mass is granulated. The granulate is dried in a fluidizing drying equipment at 25°30° C. The mixture is then regranulated on a 16 mesh sieve. After regranulation the granulate is further dried in a fluidizing drier until the humidity content will decrease to 2%. The granulate containing at most 2% humidity is compressed preferably with a rotary tabletting machine to biconvex dragee cores of a diameter of 13 mm.

The coating is carried out by methods known per se by film-tablet coating method in over-pressure equipment. By using dragée coloring the composition is coated with colored coating in order to differentiate between the compositions. The humidity content of the coated tablets may be at most 2.5%.

Components needed to 15 000 pieces of dragée cores:

| | | |
|---|---|---|
| I. | Rimazolium sulphate | 9.00 kg. |
| | microcrystalline cellulose | 1.48 kg. |
| | hydrophobic colloidal silicic acid | 0.96 kg. |
| | colloidal silicic acid | 0.15 kg. |
| | betaine in hydrochloric acid | 0.09 kg. |
| II. | stearine | 1.50 kg. |
| | polyvinyl pyrrolidone vinyl acetate | 1.02 kg. |
| | isopropanol | 3.00 kg. |
| | | 17.20 kg. |

Note:
9.0 kg. of Rimazolium methylsulphate refers to 100% active ingredient content. According to the active ingredient content of the batch the deviations are corrected by changing the weight of the microcrystalline cellulose.

EXAMPLE 2

The dragée core according to Example 1 is compressed with a biconvex ellipsoid tool, the small axis of the ellipsoid of which is at least 2.5-3 times smaller than the big axis.

EXAMPLE 3

Preparation of time-release Probon dragée cores containing 400 mg. of active ingredient Dragée core -continued

| | | |
|---|---|---|
| I. | Rimazolium methylsulphate | 400.0 mg. |
| | betaine in hydrochloric acid | 4.0 mg. |
| | colloidal silicic acid | 6.7 mg. |
| | hydrophobic colloidal silicic acid | 42.6 mg. |
| | microcrystalline cellulose | 65.4 mg. |
| II. | polyvinyl pyrrolidone vinyl acetate | 45.4 mg. |
| | stearine | 66.6 mg. |
| | | 630.7 mg. |
| | Dragée shell | |
| | talc | 31.9 mg. |
| | polyvinyl pyrrolidone vinyl acetate | 10.0 mg. |
| | methyl cellulose | 10.0 mg. |
| | titanium dioxide | 5.1 mg. |
| | polyoxyethylene 6000 | 1.3 mg. |
| | | 58.3 mg. |

Technology

One may proceed according to Examples 1 and 2. If a dragée core having disc form is pressed with a biconvex tool, dragée cores having a diameter of 12 mm. are preferably prepared.

EXAMPLE 4

Preparation of Probon-Indomethacin time-release combined dragée

| | | |
|---|---|---|
| | Dragée core | |
| I. | Rimazolium methyl sulphate | 400.0 mg. |
| | indomethacin | 20.0 mg. |
| | betaine in hydrochloric acid | 4.0 mg. |
| | colloidal silicic acid | 6.7 mg. |
| | hydrophobic colloidal silicic acid | 42.6 mg. |
| | microcrystalline cellulose | 65.4 mg. |
| II. | polyvinyl pyrrolidone vinyl acetate | 45.4 mg. |
| | stearine | 66.6 mg. |
| | | 650.7 mg. |
| | Dragée shell | |
| | talc | 32.9 mg. |
| | polyvinyl pyrrolidone vinyl acetate | 10.4 mg. |
| | methyl cellulose | 10.4 mg. |
| | titanium dioxide | 5.3 mg. |
| | polyoxyethylene 6000 | 1.3 mg. |
| | | 60.3 mg. |

Technology is identical with that of described in Example 3. (We note that indomethacine is homogenized with the mixture I. according to Example 1. during preparation.)

EXAMPLE 5

Preparation of Probon-Azidocodeine time-release combined dragées

| | | | |
|---|---|---|---|
| | Dragée core | | |
| I. | Rimazolium methyl sulphate | 600.0 mg. | |
| | azidocodeine in the form of a bitartrate | 10.0 mg. | (14.42 mg.) |
| | betaine in hydrochloric acid | 6.0 mg. | |
| | colloidal silicic acid | 10.0 mg. | |
| | hydrophobic colloidal silicic acid | 63.9 mg. | |
| | microcrystalline cellulose | 97.9 mg. | |
| II. | polyvinyl pyrrolidone vinyl acetate | 67.9 mg. | |
| | stearine | 99.8 mg. | |
| | | 955.5 mg. | |

The composition of the dragée shell and the technology are the same as described in Example 1.

EXAMPLE 6

1,6-Dimethyl-3-ureido-4-oxo-1,6,7,8-tetrahydro-4H-pyrido[1,2-a]pyrimidine

| Dragée core | | |
|---|---|---|
| I. | 1,6-Dimethyl-3-ureido-4-oxo-1,6,7,8-tetra-hydro-4H—pyrido[1,2-a]pyrimidine betaine in hydrochloric acid | 100.0 mg. |
| | | 1.0 mg. |
| | colloidal silicic acid | 1.6 mg. |
| | hydrophobic colloidal silicic acid | 10.6 mg. |
| | microcrystalline cellulose | 16.3 mg. |
| II. | polyvinyl pyrrolidone vinyl acetate | 11.3 mg. |
| | stearine | 16.6 mg. |
| | | 157.4 mg. |
| Dragée shell | | |
| | talc | 8.0 mg. |
| | polyvinyl pyrrolidone vinyl acetate | 2.5 mg. |
| | methyl cellulose | 2.5 mg. |
| | titanium dioxide | 1.3 mg. |
| | polyoxyethylene 6000 | 0.3 mg. |
| | | 14.6 mg. |

Technology is the same as described in Example 1. Preferably biconvex dragée cores are prepared having a diameter of 8 mm.

EXAMPLE 7

Preparation of time-release Probon dragées stabilized with citric acid having an active ingredient content of 600 mg

| Dragée core | | |
|---|---|---|
| I. | Rimazolium methyl sulphate | 600.0 mg. |
| | citric acid | 33.6 mg. |
| | colloidal silicic acid | 10.0 mg. |
| | hydrophobic colloidal silicic acid | 63.9 mg. |
| | microcrystalline cellulose | 94.3 mg. |
| II. | polyvinyl pyrrolidone vinyl acetate | 67.9 mg. |
| | stearine | 90.8 mg. |
| | | 960.6 mg. |
| dragée shell | | |
| | talc | 48.5 mg. |
| | polyvinyl pyrrolidone vinyl acetate | 15.1 mg. |
| | methyl cellulose | 15.1 mg. |
| | titanium dioxide | 7.8 mg. |
| | polyoxyethylene 6000 | 2.0 mg. |
| | | 88.5 mg. |

Technology is the same as described in Example 1.

EXAMPLE 8

Preparation of time-release CH 123 dragée containing 200 mg. active ingredient

| Dragée core | | |
|---|---|---|
| I. | CH 123 | 200.0 mg. |
| | citric acid | 11.2 mg. |
| | colloidal silicic acid | 3.3 mg. |
| | hydrophobic silicic acid | 21.3 mg. |
| | microcrystalline cellulose | 31.4 mg. |
| II. | polyvinyl pyrrolidone vinyl acetate | 22.6 mg. |
| | stearine | 30.2 mg. |
| | | 320.0 mg. |
| Dragée shell | | |
| | talc | 15.9 mg. |
| | polyvinyl pyrrolidone vinyl acetate | 5.0 mg. |
| | methyl cellulose | 5.0 mg. |
| | titanium dioxide | 2.5 mg. |
| | polyoxyethylene 6000 | 0.6 mg. |
| | | 29.0 mg. |

| -continued | |
|---|---|
| weight of 1 dragée | 349.0 mg |

EXAMPLE 9

Preparation of time-release CH 150 dragée having 150 mg. of active ingredient

| Dragée core | | |
|---|---|---|
| I. | CH 150 | 150.0 mg. |
| | tartaric acid | 8.5 mg. |
| | colloidal silicic acid | 4.0 mg. |
| | hydrophobic silicic acid | 17.0 mg. |
| | microcrystalline cellulose | 25.0 mg. |
| II. | polyvinyl pyrrolidone vinyl acetate | 20.0 mg. |
| | stearine | 23.5 mg. |
| | | 248.0 mg. |
| Dragée shell | | |
| | talc | 12.3 mg. |
| | polyvinyl pyrrolidone vinyl acetate | 3.9 mg. |
| | methyl cellulose | 3.9 mg. |
| | titanium dioxide | 2.0 mg. |
| | polyoxyethylene 6000 | 0.4 mg. |
| | | 22.5 mg. |
| weight of 1 dragée | | 270.5 mg. |

Rimazolium methylsulphate: 1,6-dimethyl-3-carbethoxy-4-oxo-6,7,8,9-tetrahydro-homopyrimidazolium metosulphate
Active ingredient of Probon: Rimazolium methylsulphate.

We claim:
1. A tablet or dragee core for a time-release pharmaceutical composition, suitable for oral administration, which comprises as active ingredient 50 to 70% by weight of a compound of the formula (I)

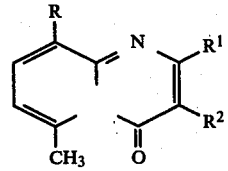

or the formula (Ia)

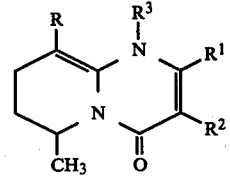

wherein
R is hydrogen or —CH$_2$COOH,
R$^1$ is hydrogen or alkyl having 1 to 4 carbon atoms,
R$^2$ is alkyl having 1 to 4 carbon atoms, alkoxycarbonyl having 2 to 5 carbon atoms, carbamoyl or ureido,
R$^3$ is hydrogen or methyl, and the dotted line stands for two hydrogens or another bond, or a pharmaceutically acceptable acid addit ion or quaternary ammonium salt thereof, and which further comprises by weight
1% colloidal silicic acid,
6.5% hydrophobic colloidal silicic acid,
7 to 12% fatty acid,
8 to 12% microcrystalline cellulose,
4 to 9% polyvinylpyrrolidone-vinyl acetate, and 0.5 to 4% of an acid stabilizer selected from the group consisting of betaine in hydrochloric acid tartaric acid and citric acid.

2. The table or dragee core defined in claim 1 wherein the fatty acid is stearic acid present in the amount of 10.5%, the microcrystalline cellulose is present in an amount of 10%, the polyvinylpyrrolidone-vinyl acetate is present in an amount of 7% and the acid stabilizer is selected from the group consisting of 0.6% betaine in hydrochloric acid and 3.5% citric acid.

3. The dragee core defined in claim 1 coated by a shell which comprises 55% by weight talc, 17% by weight polyvinylpyrrolidone-vinyl acetate, 17% by weight cellulose, 9% by weight titanium dioxide, and 2% by weight polyoxyethylene 6000.

4. The time-release pharmaceutical composition defined in claim 1 further comprising an inert filling agent or diluent.

5. The time-release pharmaceutical composition defined in claim 1 which comprises 1,6-dimethyl-3-carbethoxy-4-oxo-6,7,8,9-tetrahydro-homopyrimidzaolium metosulfate of the formula (I) as active ingredient.

6. The time-release pharmaceutical composition defined in claim 1 which comprises 6-methyl-9-carboxymethyl-4-oxo-6,7,8,9-tetrahydro-4H-pyrido(1,2-a)pyrimidine of the formula (I) as active ingredient.

7. The time-release pharmaceutical composition defined in claim 1 which comprises 2,6-dimethyl-3-ethyl-4-oxo-4H-pyrido(1,2-a)pyrimidine hydrochloride of the formula (I) as active ingredient.

8. The time-release pharmaceutical composition defined in claim 1 which comprises 2,6-dimethyl-3-ethyl-4-oxo-1,6,7,8-tetrahydro-4H-pyrido(1,2-a)pyrimidine hydrochloride of the formula (Ia) as active ingredient.

9. The time-release pharmaceutical composition defined in claim 1 which comprises 1,6-dimethyl-3-ureido-4-oxo-1,6,7,8-tetrahydro-4H-pyrido(1,2-a)pyrimidine of the formula (Ia) as active ingredient.

10. The time-release pharmaceutical composition defined in claim 1 which comprises 1,6-dimethyl-3carbethoxy-4-oxo-6,7,8,9-tetrahydro-homopyrimidazolium-metosulfate of the formula (I) and indomethacin as active ingredients.

11. The time-release pharmaceutical composition defined in claim 1 which comprises 1,6-dimethyl-3-carbethoxy-4-oxo-6,7,8,9-tetrahydro-homopyrimidazolium-metosulfate of the formula (I) and azidocodeine bitartrate as active ingredients.

12. The time-release pharmaceutical composition defined in claim 1 in the form of a tablet or dragee, containing up to 2.5% by weight of water.

* * * * *

UNITED STATES PATENT AND TRADEMARK OFFICE
CERTIFICATE OF CORRECTION

PATENT NO. : 4,434,152
DATED : 28 February 1984
INVENTOR(S) : Tibor HORVATH et al It is certified that error appears in the above-identified patent and that said Letters Patent is hereby corrected as shown below:

In the heading, left column, change item [54] to read

-- TIME-RELEASE ORAL PHARMACEUTICAL COMPOSITIONS--.

In the claims, claim 1,

Change Formula (I) to read:

--

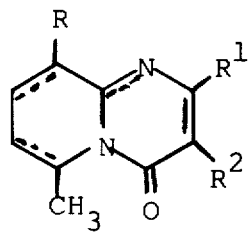

--.

Signed and Sealed this

Thirtieth Day of April 1985

[SEAL]

Attest:

DONALD J. QUIGG

Attesting Officer     Acting Commissioner of Patents and Trademarks